United States Patent [19]

Confalone et al.

[11] 4,428,963

[45] Jan. 31, 1984

[54] NOVEL THIOPHENE DERIVATIVES

[75] Inventors: Pasquale N. Confalone, West Caldwell; Giacomo Pizzolato, Glen Ridge; Milan R. Uskokovic, Upper Montclair, all of N.J.; Marianne Rouge, Basel, Switzerland

[73] Assignee: Hoffmann-La Roche Inc., Nutley, N.J.

[21] Appl. No.: 474,072

[22] Filed: Mar. 10, 1983

Related U.S. Application Data

[60] Division of Ser. No. 318,779, Nov. 6, 1981, abandoned, which is a division of Ser. No. 111,637, Jan. 14, 1980, Pat. No. 4,317,915, which is a continuation-in-part of Ser. No. 889,459, Mar. 23, 1978, abandoned, which is a continuation-in-part of Ser. No. 820,521, Aug. 1, 1977, abandoned, which is a continuation-in-part of Ser. No. 716,853, Aug. 23, 1976, abandoned.

[51] Int. Cl.$^3$ ............................................. A61K 31/38
[52] U.S. Cl. .................................................... 424/275
[58] Field of Search ........................... 424/275; 549/68

[56] References Cited

U.S. PATENT DOCUMENTS

| | | |
|---|---|---|
| 2,443,598 | 6/1948 | Cheney . |
| 2,502,421 | 4/1950 | Cheney . |
| 2,502,423 | 4/1950 | Cheney . |
| 2,502,424 | 4/1950 | Cheney . |
| 3,076,817 | 2/1963 | Fieselmann . |
| 3,445,473 | 5/1969 | Ruschig et al. . |
| 3,795,681 | 3/1974 | Ruschig et al. . |
| 3,823,161 | 7/1974 | Lesser . |
| 3,828,001 | 8/1974 | Brood . |
| 3,855,243 | 12/1974 | Ruschig et al. . |
| 3,903,289 | 9/1975 | Magee . |
| 3,929,833 | 12/1975 | Krieger et al. . |
| 3,963,750 | 6/1976 | Goudie . |
| 3,978,084 | 8/1976 | Confalone et al. . |
| 4,317,915 | 3/1982 | Confalone et al. ............... 549/68 |

FOREIGN PATENT DOCUMENTS

| | | |
|---|---|---|
| 574279 | 12/1945 | United Kingdom . |
| 608969 | 9/1948 | United Kingdom . |
| 837086 | 6/1960 | United Kingdom . |
| 1133850 | 11/1965 | United Kingdom . |
| 1278084 | 6/1972 | United Kingdom . |

OTHER PUBLICATIONS

Baker et al., Jour. Org. Chem., vol. 18, pp. 138–152 (1953) Particularly pp. 138–139 and 145 (Compounds IV and VII).

Arzneim. Forsch., vol. 22, pp. 2146–2147 (1972) (English Language Summary at p. 2147, bottom of column).

*Primary Examiner*—Alan Siegel
*Attorney, Agent, or Firm*—Jon S. Saxe; Bernard S. Leon; George W. Johnston

[57] ABSTRACT

Thiophene derivatives having utility as blood lipid lowering agents and as antiobesity agents are disclosed.

10 Claims, No Drawings

NOVEL THIOPHENE DERIVATIVES

CROSS REFERENCE TO RELATED APPLICATIONS

This is a divisional of application Ser. No. 318,779, filed Nov. 6, 1981, now abandoned, which in turn is a divisional of Ser. No. 111,637, filed Jan. 14, 1980, now U.S. Pat. No. 4,317,915, which in turn is a continuation-in-part application of Ser. No. 889,459, filed Mar. 23, 1978, now abandoned, which in turn is a continuation-in-part application of Ser. No. 820,521, filed Aug. 1, 1977, now abandoned, which in turn is a continuation-in-part application of Ser. No. 716,853, filed Aug. 23, 1976, now abandoned.

SUMMARY OF THE DISCLOSURE

This invention is directed to compounds of the formula:

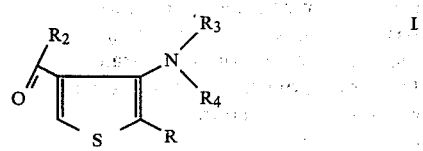

wherein R is lower alkyl; $R_2$ is hydrogen, hydroxy, lower alkoxy, or amino; $R_3$ and $R_4$, which may be the same or different, are lower alkyl, aryl, aralkyl, acyl and hydrogen; or a pharmaceutically acceptable salt thereof.

The compounds are useful as blood lipid lowering agents and as antiobesity agents.

Usage of the compounds within the scope of formula I has resulted in significant lowering of lipid levels and reduction in body weight of warm-blooded animals.

BACKGROUND OF THE INVENTION

Atherosclerosis, a form of arteriosclerosis, is characterized by internal thickening of the major blood vessels due to localized accumulation of lipids, of which cholesterol and triglycerides, comprise the major constituents. Furthermore, it has been found that those suffering from the disease exhibit abnormally high blood cholesterol levels. While the etiology of the disease is not fully understood, it is believed that cholesterol plays an important role. A high level of blood triglycerides is also a risk factor for atherosclerosis. (The Heritable Hypolipoproteinemias and Atherosclerosis, C. J. Glueck and R. W. Fallat, Lipids, Lipoproteins and Drugs, pp. 169–183 and 305–316, Plenum Press, 1975.

In the advanced stages of the disease, plaques, comprising cholesterol and other β-lipoproteins, accumuate in the aorta coronary, cerebral, and peripheral arteries of the lower extremities. As these plaques increase in size the danger of fibrin deposition, possibly resulting in thrombosis and occlusion, is enhanced.

While no sure method has been found for preventing the disease, it has been recommended that dietary habits be observed that will insure low β-lipoprotein levels. Besides stringent dietary management, various therapeutic agents such as estrogens, thyroxine analogs and sitosterol preparations have been used to lower the cholesterol levels of those afflicted with the condition.

It has now been found that various thiophene derivatives are effective hypolipemic agents because of their ability to lower the blood lipid level of warm blooded animals. Consequently, these compounds can be expected to be useful in the treatment of atherosclerosis and related cardiovascular diseases which are associated with elevated blood lipid levels.

Obesity represents a state of increased body fat which may decrease longevity, aggravate the onset and progression of other diseases, (e.g., heart disease, diabetes, gallstones) and impact on one's social or economic status. (The Obese Patient, G. A. Bray, Vol. IX in the series "Major Problems in Internal Medicine", W. B. Saunders Co., 1976.)

It has also been found that the thiophene compounds of the invention selectively reduce body fat by suppressing its biosynthesis and thus are useful in the treatment of obesity.

DETAILED DESCRIPTION OF THE INVENTION

As used throughout this application, the term "lower alkyl" denotes straight and branched chain, saturated aliphatic alkyl groups having from 1 to 8 carbon atoms, such as methyl, ethyl, propyl, isopropyl and the like. The term "lower alkoxy" denotes saturated straight or branched chain alkoxy groups having from 1 to 8 carbon atoms, such as methoxy, ethoxy, propoxy, isopropoxy and the like. The term "halogen" includes all four halogens, i.e., chlorine, bromine, iodine, and fluorine. The term "acyl" refers to acyl groups having attached thereto lower alkyl, aryl, aralkyl and alkoxy moieties. Typical acyl groups include benzoyl, acetyl, propionyl, carbomethoxy and the like. The term "aryl" denotes mono-nuclear aryl groups such as unsubstituted or substituted phenyl, said substitutions being in one or more positions and selected from lower alkyl, trihalomethyl, such as trifluoro and trichloro methyl, aralkyl, halogen, lower alkoxy, amino, nitro, mono and di-lower alkylamino. The term "amino" as used herein includes unsubstituted and substituted amino groups wherein said substituents may be lower alkyl, acyl, aryl or aralkyl. The term "alkali metal" denotes metals such as sodium, potassium, lithium and the like. The term "alkanol" as used herein, denotes straight or branched chain alcohols having 1–20 carbon atoms. The term "lower alkanols" denotes alkanols having 1–6 carbon atoms. The term "alkoxide" as used herein, refers to metal salts, preferably alkali and alkaline earth metal salts of alkanols. The term "alkaline earth metal" refers to calcium, barium, magnesium and the like. The term "aralkyl" connotes groups wherein aryl and lower alkyl are as described above.

In accordance with this invention, the thiophene of formula I is obtained by initially reacting a compound of the formula:

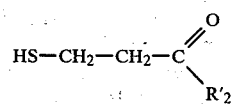

with a compound of the formula:

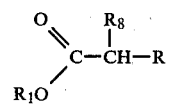

to form a compound of the formula:

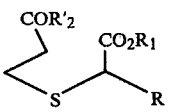

wherein R is as previously defined, $R_1$ is lower alkyl, $R'_2$ is lower alkoxy and $R_8$ is halogen, mesyloxy and tosyloxy.

The foregoing reaction is carried out in the presence of a lower alkanol and an alkali metal alkoxide, preferably methanol and sodium methoxide. Although temperature and pressure are not critical, this reaction is generally carried out at atmospheric pressure and temperature of from about 15° C. to about 60° C., preferably 25° C.

Compound IV is then treated with an alkali metal alkoxide, preferably sodium methoxide in the presence of an aromatic hydrocarbon, preferably benzene to form a compound of the formula:

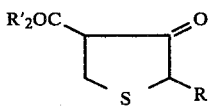

wherein R and $R'_2$ are as defined above. Although temperatures and pressures are not critical, this reaction is generally carried out at atmospheric pressure and a temperature of from about 15° C. to about 60° C., preferably 25° C.

Compound V is then transformed to an oxime of the formula:

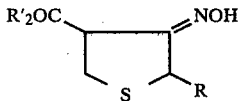

wherein R and $R'_2$ are as defined above. Any conventional method of preparing an oxime from a keto compound can be used to convert the 4,5-dihydrothiophene of formula V to the oxime of formula VI. Preferably, the 4,5-dihydrothiophene of formula V is treated with a hydroxylamine hydrohalide, preferably hydroxylamine hydrochloride, in a nitrogen-containing base. In carrying out this reaction, any conventional nitrogen-containing base can be utilized. The preferred nitrogen-containing bases are the amines. Among the amines which can be utilized are the primary amines, such as the loweralkylamines, particularly methylamine, ethylamine, and aniline; the secondary amines, such as the diloweralkylamines, particularly dimethylamine and diethylamine, and pyrrole; and the tertiary amines, such as the triloweralkylamines, particularly trimethylamine and triethylamine, pyridine and picoline. Also, in carrying out this reaction with a hydroxylamine hydrohalide, temperature and pressure are not critical, and the reaction can be suitably carried out at from room temperature to reflux and at atmospheric pressure. Preferably, this reaction is carried out at room temperature (about 22° C.). Further, this reaction can be carried out in an inert organic solvent. In this reaction any conventional inert organic solvent can be utilized, such as the aliphatic or aromatic hydrocarbons, as for example n-hexane or benzene. Preferably, this reaction is carried out in an excess of the nitrogen-containing base, which serves as the solvent medium.

The oxime of formula VI is converted to an amine of the formula:

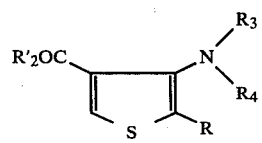

wherein R and $R'_2$ are as above, $R_3$ and $R_4$ are hydrogen. This reaction is suitably carried out by treating the oxime of formula VI with an acid, preferably a hydrohalide, in an inert, organic solvent under substantially anhydrous conditions. This reaction can be carried out preferably by treating the oxime of formula VI with hydrogen chloride. In carrying out this reaction, any conventional inert organic solvent can be utilized. The preferred inert organic solvents are the ethers, particularly the dilower alkyl ethers, such as diethyl ether, and the cyclic ethers, such as tetrahydrofuran and dioxane. In carrying out this reaction, temperature and pressure are not critical, and this reaction can be suitably carried out at from 0° C. to about 70° C. and at atmospheric pressure. Preferably, this reaction is carried out at room temperature. Where it is desired that $R_3$ and/or $R_4$ be lower alkyl or lower acyl, these moieties may be introduced by conventional procedures for converting an aromatic primary amine to N-alkyl and N-acyl derivatives. For example, treatment of compound VII with a carboxylic acid anhydride or halide in the presence of base affords the corresponding N-acyl derivatives of compound VII. The N-acyl derivatives then may be reduced preferably with a hydride reducing agent such as diborane and an inert solvent such as ether (e.g., tetrahydrofuran). Such reductions afford the N-alkyl derivatives of compound VII.

Typical carboxylic acid anhydrides and halides are acidic anhydride, acetyl chloride and benzoyl chloride. Suitable bases illustratively include organic tertiary amines such as pyridine and triethylamine.

Compound VII, where $R'_2$ is lower alkoxy, may then be converted to a compound of the formula:

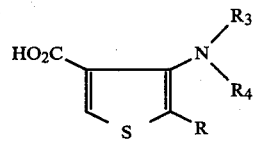

wherein R, $R_3$ and $R_4$ are as previously defined. In carrying out this reaction, any conventional method of basic hydrolysis can be utilized. This hydrolysis can be suitably carried out in a conventional inert organic solvent. The preferred solvents are the lower alkanols, particularly methanol and ethanol, and the aqueous ether solvents, preferably the aqueous dilower alkyl ethers, particularly diethyl ether, and the aqueous cyclic ethers, particularly tetrahydrofuran and dioxane. In this reaction, any conventional base can be utilized. Among the preferred bases are the alkali metal hydroxides, such as sodium, potassium and lithium hydroxide, and the alkaline earth metal hydroxides, such as barium, calcium and magnesium hydroxide, especially the alkali metal hydroxides. In this hydrolysis, temperature and pressure are not critical, and this reaction can be suitably carried out at from about 0° C. to about 100° C. and at atmospheric pressure. Preferably, this reaction is carried out at reflux, especially at about 70° C.

Compound VII and/or compound VIII may be transformed to its corresponding aldehydes, amides or esters by conventional methods for converting esters or acids to the aforementioned compounds.

For example, treatment of compound VIII with a lower alkanol (e.g., methanol, ethanol and isopropyl) or arylalkanol (e.g., benzyl alcohol) in the presence of an acid catalyst (Fisher esterification) affords corresponding lower alkyl or arylalkyl esters of formula VII.

Suitable acid catalyst include hydrogen halides, preferably hydrogen chloride. The above reaction may occur within an approximate temperature range of 60° to 150° C. but is preferably carried out at the boiling point of the alcohol which is utilized.

As previously mentioned, the herein described thiophene derivatives as well as their pharmaceutically acceptable salts, lower alkyl esters and amides, are effective hypolipidemic agents, i.e., they lower the blood lipid level of mammals. This property has been dramatically demonstrated in rats, groups, each comprising animals, of normal female Charles River rats weighing from 150–180 g. are first fed a corn oil-glucose mixture for several days and then dosed with typical compounds disclosed herein in gum arabic or water either orally or parenterally. The mechanism by which the thiophene derivatives lower body weight (antiobesity activity) and blood lipids (hypolipidemic activity) appears to be through inhibition of lipid synthesis. Potent inhibition by the compounds disclosed herein of fatty acid and cholesterol synthesis was demonstrated in rat hepatocytes in vitro and in rat liver in vivo (see below, Tables I, II, IV, V and VI). Lowered blood lipid levels were the result of decreased biosynthesis. Blood cholesterol (Table VII) and triglyceride levels (Table III and Table VII) were reduced significantly by the oral or parenteral of these compounds.

The compounds described herein can be administered parenterally as well as orally. For purposes of parenteral administration, solutions and suspensions of the herein described compounds in water or gum arabic can be employed. Of particular suitability are sterile aqueous solutions of the corresponding water-soluble salts previously described. These dosage forms are especially suitable for peritoneal injection purposes. The aqueous solutions, including those of the salts dissolved in pure distilled water, are additionally useful for intravenous injection purposes provided that their pH be properly adjusted beforehand. Such solutions should also be suitably buffered, if necessary, and the liquid diluent first rendered isotonic with sufficient saline or glucose. In this connection, the sterile aqueous media employed are readily obtained by standard techniques well known to those in the art. For instance, distilled water is ordinarily used as the liquid diluent.

The dosage required to lower the blood lipid level will be determined by the nature and the extent of the symptoms. Generally, small dosages will be administered initially with a gradual increase in dosage until the optimum leel is determined. It will generally be found that when the composition is administered orally, larger quantities of the active ingredient will be required to produce the same level as produced by a smaller quantity administered parenterally. In general, from about 0.1 to 200 mg. of active ingredient per kilogram of body weight administered in single or multiple dosage units significantly lowers the blood lipid level or body fat level.

As previously mentioned, the compounds disclosed and claimed herein are also useful as antiobesity agents. This property has been dramatically demonstrated in high fat fed Charles River rats. Groups of 10 rats were fed ad libitum a 10% corn oil, 60% glucose diet in accordance with the methodology described in Sullivan et al., Am. J. Clin. Nutr. 30:767–776 (1977). The effect of 4-amino-5-ethyl-3-thiophene carboxylic acid methyl ester hydrochloride on body weight, total body fat and protein was determined. The results are tabulated in Example 35 (Table VIII and Table IX) of the specification.

Table VIII demonstrates that the above compound significantly reduces body weight gain in high fat fed rats. Table IX illustrates that the decreased weight gain resulting from the compound is caused by selective reductions in carcass fat of the high fat fed rats. The data illustrates the dramatic antiobesity activity of the inventive thiophenes.

The dosage required for antiobesity activity is determined by the nature and the extent of obesity. Generally, small dosages will be administered initially with a gradual increase in dosage until the optimum level is determined. In general, from about 0.1 to 200 mg. of active ingredient per kilogram of body weight administered in single or multiple dosage units significantly lowers body weight. The preferred daily dose of active ingredient is 0.1 to 20 mg. per kilogram of body weight administered in single or multiple dose units.

The following non-limiting examples further illustrate this invention. All temperatures are in degrees Centigrade and the ether used is diethyl ether.

EXAMPLE 1

A solution of 116.55 g (0.971 mole) of methyl-3-mercaptopropionate in 220 ml of dry methanol at −20° was treated with 52.46 g (0.971 mole) of sodium methoxide. After 20 minutes, a solution of 203.0 g (0.971 mole) of ethyl-2-bromovalerate in 150 g of dry methanol was added dropwise. The reaction was allowed to warm to room temperature and stirred overnight. The methanol was evaporated and the residue was partitioned between ether/water. The organic phase was washed with 10% bicarbonate solution and water. After drying over magnesium sulfate, the ether was evaporated to yield 130 g (0.524 mole, 54%) of methyl-4-thia-5-carbomethoxyoctanoate as a colorless oil.

EXAMPLE 2

To a suspension of 54.0 g (1.0 mole) of sodium methoxide in 500 ml of anhydrous benzene was added dropwise at 25°, 130 g (0.524 mole) of methyl-4-thia-5-carbomethoxyoctanoate. The mixture was stirred overnight and poured into ice-water. The aqueous phase was extracted with benzene/ether, 1:1, and then acidified to pH 1 with 6 N HCl. The product, which partially separates from the water at this point, is taken up in methylene chloride. The aqueous layer is further extracted with methylene chloride. The combined organic phases are dried and evaporated to yield 94.0 g. (0.466 mole, 89%) of pure 4-carbomethoxy-3-keto-2-propyl-tetrahydrothiophene as a colorless oil.

EXAMPLE 3

A solution of 94.0 g (0.465 mole) of 4-carbomethoxy-3-keto-2-propyl-tetrahydrothiophene in 250 ml of dry pyridine was treated with 40.0 (0.576 mole) of hydroxylamine hydrochloride at 25°. The reaction was stirred overnight at room temperature. The solvent was evaporated and the residue was partitioned between 1 N HCl and methylene chloride. The organic phase was dried over sodium sulfate and evaporated to afford 100 g. (0.461 mole, 99%) of pure 4-carbomethoxy-3-keto-2-propyl-tetrahydrothiophene oxime as a colorless oil.

EXAMPLE 4

Gaseous hydrogen chloride was bubbled into one liter of anhydrous ether in which 100.0 g (0.461 mole) of 4-carbomethoxy-3-keto-2-propyl-tetrahydrothiophene oxime had been dissolved. This process was carried out at 0° for one hour. The reaction flask was stoppered with a drying tube and allowed to stir at room temperature overnight. The solvent was evaporated until the product crystallized. The white solid was collected by filtration and washed well with ether to afford 60.0 g (0.255 mole, 55%) of 3-amino-4-carbomethoxy-2-N-propylthiophene hydrochloride, m.p. 178°–180°. The product was recrystallized from methanol/ether to yield 50.0 g (0.212 mole, 46%) of pure 3-amino-4-carbomethoxy-2-n-propylthiophene hydrochloride, m.p. 180°–181°.

EXAMPLE 5

Fatty Acid and Cholesterol Synthesis in Isolated Hepatocytes

Female Charles River rats are fasted 48 hours, then meal fed a 1% corn oil, 70% glucose diet for 7 to 14 days from 8–11 a.m. The isolated rat hepatocytes are prepared by perfusing the liver in situ. The hepatocytes are incubated in an oscillating water bath at 37° C. for 60 minutes. Each flask contains a total of 2.1 ml volume, consisting of 1 ml isolated rat hepatocytes (10–20 mg dry weight cells), 1 ml Krebs-Henseleit bicarbonate buffer pH 7.4, 16.5 mM glucose, 1 μmole L-alanine, 1 μCi [U-$^{14}$C]alanine, 1 mCi $^3$H$_2$O, and 2 mM inhibitor in H$_2$O or DMSO at $p^H$ 7.4 (unless otherwise specified). All incubations are done in triplicate and all experiments are repeated at least twice. CO$_2$ is collected in each flask following the 60 minutes incubation by adding 0.3 ml ethanolamine:2-methoxy-ethanol (1:2) to the center well, 0.4 ml of 62.5% citric acid to the cell media, and incubating for 45 minutes. The contents of the center well are transferred to scintillation counting fluid and $^{14}$CO$_2$ content is determined. The media is saponified, acidified (only for determining the rate of lipogenesis) and extracted with hexane. At this stage the lipids are either counted (to determine the rate of lipogenesis) or precipitated with digitonin, washed, and counted (to determine the rate of cholesterogenesis). The conversion of $^3$H$_2$O and [$^{14}$C]alanine into fatty acids or sterols is determined in a PDS/3, Mark II liquid scintillation counting system. Data are expressed as nmoles $^3$H$_2$O and [$^{14}$C]alanine converted into fatty acids or cholesterol, and nmoles [$^{14}$C]alanine oxidized to $^{14}$CO$_2$ per mg dry weight cells per 60 minutes. The results are set forth in Table I.

TABLE I

EFFECT OF 3-AMINO-4-CARBOMETHOXY-2-N—PROPYLTHIOPHENE HYDROCHLORIDE ON LIPID SYNTHESIS AND CO$_2$ PRODUCTION IN ISOLATED RAT HEPTOCYTES[a]

| Treatment | Dose nM | Fatty Acid Synthesis | | Cholesterol Synthesis | | CO$_2$ Production |
|---|---|---|---|---|---|---|
| | | $^3$H$_2$O | [$^{14}$C]alanine converted | $^3$H$_2$O converted | [$^{14}$C]alanine | [$^{14}$C]alanine converted |
| | | AS % OF CONTROL | | | | |
| Control (DMSO) | — | 100 | 100 | 100 | 100 | 100 |
| 3-Amino-4-carbo- | 0.50 | 17* | 9* | 28* | 19* | 49* |
| methoxy-2-n-propyl- | 0.25 | 21* | 10* | 29* | 21* | 50* |
| thiophene hydro- | 0.10 | 18* | 10* | 35* | 23* | 53* |
| chloride | 0.05 | 18* | 11* | 33* | 26* | 54* |
| | 0.01 | 30* | 19* | 49* | 31* | 73* |

[a]Each flask contained 13.7 mg cells dry weight and 25 μl DMSO. Each value is the mean of 2 to 14 determinations.
*Statistically different from control value.

EXAMPLE 6

Fatty Acid and Cholesterol Synthesis In Vivo

Rats are prepared by fasting 48 hours and refeeding a 1% corn oil 70% glucose diet for several days (5–15). On the experimental day, rats are dosed 30 or 60 minutes before the 3 hour meal by oral intubation, or 60 minutes after the end of the 3 hour meal by intraperitoneal injection. (The dose concentrated is a mmoles/kg-/5–10 ml H$_2$O or 1% gum arabic depending on the solubility of the compound.) Rats are sacrificed by decapitation after a 30 minute pulse consisting of: 1mCi$^3$H$_2$O,5 μCi[U-$^{14}$C]alanine, 12.3 mg. alanine, and 30.6 mg α-ketoglutaric acid in 0.25 mg saline, given at the end of the 3 hour meal by i.v. injection into the tail vein. Blood was collected, allowed to clot and the serum analyzed for triglyceride and cholesterol levels. The livers are quickly excised, saponified, and acidified (only for determining the rate of lipogenesis) and extracted with hexane. At this stage the lipids are either counted (to determine the rate of lipogenesis) or precipitated with digitonin, washed, and counted (to determine the rate of cholesterogenesis). The conversion of $^3$H$_2$O and [$^{14}$C]alanine into fatty acids or sterols is determined in a PDS/3, Mark II liquid scintillation counting system. Data are expressed as moles $^3$H$_2$O nmoles converted into fatty acids and cholesterol per g liver per 30 minutes. The results are set forth in Tables II-VII.

TABLE II

EFFECT OF INTRAPERITONEAL ADMINISTRATION OF 3-AMINO-4-CARBOMETHOXY-2-N—PROPYLTHIOPHENE HYDROCHLORIDE ON IN VIVO LIPOGENESIS AND CHOLESTEROGENESIS

| Treatment[a] | Dose mmoles/kg | Fatty Acid Synthesis[b] nmoles[$^{14}$C]alanine converted/g/30 min. | Cholesterol Synthesis[b] $\mu$moles $^3H_2O$ converted/g/30 min. | nmoles[$^{14}$C]alanine converted/g/30 min |
|---|---|---|---|---|
| Control (1% gum arabic) | — | 614 ± 66 | 1.36 ± 0.07 | 35.7 ± 3.2 |
| 3-Amino-4-carbomethoxy-2-n-propylthiophene hydrochloride | 0.1 | 251 ± 36** | 0.85 ± 0.06*** | 17.6 ± 1.9* |

[a]Charles River CD rats (5–6 rats per group at 150–170 g) were fasted 48 hours, then meal-fed a high carbohydrate diet for 14 days. On the experimental day, the rats were given an i.p. dose of 3-amino-4-carbomethoxy-2-n-propylthiophene hydrochloride (0.1 mmoles/kg/10 ml 1% gum arabic) immediately after the 3 hour meal, followed, 30 minutes later, by an i.v. pulse. One hour after the i.p. injection the rats were sacrificed and rates of synthesis determined.
[b]Data are expressed as $\mu$moles $^3H_2O$ and moles[$^{14}$C]alanine converted into fatty acids or cholesterol per g liver per 30 minutes.
*$p > 0.05$
**$p > 0.01$
***$p > 0.001$.

TABLE III

EFFECT OF 3-AMINO-4-CARBOMETHOXY-2- N—PROPYLTHIOPHENE HYDROCHLORIDE ON SERUM LIPIDS[a]

| Treatment | Administration Route | Dose mmoles/kg | Triglycerides mg % | Cholesterol mg % |
|---|---|---|---|---|
| Control (%) gum arabic | i.p. | — | 67 ± 4 | 116 ± 7 |
| 3-Amino-4-carbomethoxy-2-n-propylthiophene hydrochloride | i.p. | 0.1 | 51 ± 3** | 105 ± 11 |

[a]Charles River CD rats (5–6 rats per group at 150–170 g) were fasted 48 hours, then meal-fed a high carbohydrate diet for 14 days. On the experimental day, the rats were given an i.p. dose of 3-amino-4-carbomethoxy-2-n-propylthiophene hydrochloride (0.1 mmoles/kg/10 ml % gum arabic) immediately after the 3 hour meal, followed, 30 minutes later, by an i.v. pulse. One hour after the i.p. injection the rats were sacrificed and rates of synthesis determined.
**$p > 0.01$.

TABLE IV

EFFECT OF ORAL ADMINISTRATION OF 3-AMINO-4-CARBOMETHOXY-2- N—PROPYLTHIOPHENE HYDROCHLORIDE ON IN VIVO FATTY ACID SYNTHESIS

| Treatment[a] | Dose mmoles/kg | Fatty Acid Synthesis[b] $\mu$moles $^3H_2O$ converted/g/30 min. | % of Control | nmoles[$^{14}$C]alanine converted/g/30 min. | % of Control |
|---|---|---|---|---|---|
| Control (1% gum arabic) | — | 19.6 ± 2.4 | 100 | 473 ± 76 | 100 |
| 3-Amino-4-carbomethoxy-2-n-propylthiophene hydrochloride | 1.2 | 7.1 ± 1.7** | 36 | 162 ± 60** | 34 |

[a]Charles River CD rats (6 rats per group at 160–180 g) were fasted 48 hours, then meal-fed a high carbohydrate diet for 18 days. On the experimental day, rats were given an oral dose (1% gum arabic or 3-amino-4-carbomethoxy-2-n-propylthiophene hydrochloride in 1% gum arabic at the above concentrations) 30 minutes before the beginning of the meal. At the end of the 3 hour meal, the rats were given an i.v. pulse, sacrificed 30 minutes later and rates of synthesis were determined.
[b]Data are expressed as $\mu$moles $^3H_2O$ and nmoles [$^{14}$C]alanine converted into fatty acids per g liver per 30 minutes.
*$p > 0.05$
**$p > 0.01$.

TABLE V

EFFECT OF ORAL ADMINISTRATION OF 3-AMINO-4-CARBOMETHOXY-2- N—PROPYLTHIOPHENE HYDROCHLORIDE ON IN VIVO CHOLESTEROL SYNTHESIS

| Treatment[a] | Dose nmoles/kg | $\mu$moles $^3H_2O$ converted/g/30 min. | % of Control | nmoles[$^{14}$C]alanine converted/g/30 min. | % of Control |
|---|---|---|---|---|---|
| Control (1% gum arabic) | — | 1.35 ± 0.04 | 100 | 33.0 ± 3.1 | 100 |
| 3-Amino-4-carbomethoxy-2-n-propylthiophene hydrochloride | 1.2 | 0.88 ± 0.16* | 65 | 15.2 ± 3.2** | 46 |
| 3-Amino-4-carbomethoxy-2-n-propylthiophene hydrochloride | 0.4 | 0.96 ± 0.05*** | 71 | 17.4 ± 0.9*** | 53 |

[a]Charles River CD rats (6 rats per group at 160–180 g) were fasted 48 hours, then meal-fed a high carbohydrate diet for 18 days. On the experimental day, rats were given an oral dose (1% gum arabic or 3-amino-4-carbomethoxy-2-n-propylthiophene hydrochloride in 1% gum arabic at the above concentrations) 30 minutes before the beginning of the meal. At the end of the 3 hour meal, the rats were given an i.v. pulse, sacrificed 30 minutes later, and rates of synthesis were determined.
[b]Data are expressed as $\mu$moles $^3H_2O$ and nmoles [$^{14}$C]alanine converted into cholesterol per g liver per 30 minutes.
*$p > 0.05$
**$p > 0.01$
***$p > 0.001$.

EXAMPLE 7

A solution of 66.29 g. (0.552 mole) methyl-3-mercaptopropionate in 50 ml. anhydrous methanol was cooled to 0° and treated with 120 ml. of a 25% solution of sodium methoxide in methanol. To this solution was added dropwise 100 g. (0.552 mole) of ethyl-2-bromopropionate in 100 ml. anhydrous methanol. The reaction was allowed to proceed at 25° overnight. The solvent was evaporated, and the residue was partitioned between ether and 10% sodium bicarbonate. The aqueous phase was further extracted with ether. The combined organic extracts were dried over magnesium sulfate and evaporated to yield 121.40 g. (100%) of 2-methyl-3-thia-1,6-hexanedionic acid-1-ethyl-6-methyl ester as a pale yellow oil.

Similarly, 61.4 g. (0.51 mole) of methyl-3-mercaptopropionate was combined with 106.8 g. (0.51 mole) of ethyl-2-bromovalerate to yield 120.91 g. (96%) of 2-isopropyl-3-thia-1,6-hexanedionic acid-1-ethyl-6-methyl ester as a colorless oil.

EXAMPLE 8

A solution of 121.4 g. (0.552 mole) of 2-methyl-3-thia-1,6-hexanedioic acid-1-ethyl-6-methyl ester in 90 ml. dry benzene was added dropwise to a suspension of 30 g. anhydrous sodium methoxide in 200 ml. dry benzene. The reaction was allowed to proceed overnight. The mixture was partitioned between water/ether. The aqueous phase was further extracted with benzene. The aqueous phase was then acidified to pH 1 with 6 N HCl and extracted three times with methylene chloride. The methylene chloride extracts were combined, dried over sodium sulfate, and evaporated to afford 79.17 g. (82%) of pure 4-carbomethoxy-3-keto-2-methyltetrahydrothiophene as a colorless oil.

Similarly, 120.91 g. of 2-isopropyl-3-thia-1,6-hexanedionic acid-1-ethyl-6-methyl ester was converted to 91.0 g. (93%) of 4-carbomethoxy-2-isopropyl-3-keto-tetrahydrothiophene as a colorless oil.

EXAMPLE 9

A solution of 37.26 g. (0.214 mole) of 4-carbomethoxy-3-keto-2-methyltetrahydrothiophene in 100 ml. anhydrous pyridine was treated with 18.0 g. (0.261 mole) hydroxylamine hydrochloride. The mixture was stirred 24 hours at 25°. The reaction was concentrated and partitioned between 1 N hydrochloric acid/methylene chloride. The aqueous phase was extracted two times with methylene chloride. The combined organic extracts were dried and evaporated to yield 40.1 g (99%) of pure 4-carbomethoxy-3-keto-2-methyltetrahydrothiophene oxime as a colorless oil.

Similarly, 52.8 g. (0.26 mole) of 4-carbomethoxy-2-isopropyl-3-keto-tetrahydrothiophene was converted to 49.0 g. (0.226 mole), 87%) of 4-carbomethoxy-2-isopropyl-3-keto-tetrahydrothiophene oxime as a colorless oil.

EXAMPLE 10

A solution of 41.1 g. (0.217 mole) of 4-carbomethoxy-3-keto-2-methyltetrahydrothiophene oxime in 600 ml. anhydrous ether, previously saturated with gaseous hydrogen chloride at 0°, was allowed to stir at 25° overnight. The separated solid was collected, washed well with ether, and dried to afford 33.2 g. Evaporation of the filtrate yielded after recrystallization of the residue an additional 4.2 g. to afford a total yield of pure 3-amino-4-carbomethoxy-2-methylthiophene hydrochloride of 37.4 g. (84%). The compound melts 191°-192°.

Similarly, 49.12 g. (0.226 mole) of 4-carbomethoxy-2-isopropyl-3-keto-tetrahydrothiophene was converted to 18.49 g. (35%) of 3-amino-4-carbomethoxy-2-isopropylthiophene hydrochloride, m.p. 185 (dec.).

EXAMPLE 11

A solution of 2.07 g (0.010 mole) of 3-amino-4-carbomethoxy-2-methylthiophene hydrochloride in 35 ml. methanol was treated with 23 ml. 1 N sodium hydroxide. The mixture was heated under reflux 0.5 hour, cooled, and poured into brine. The pH was adjusted to 5 and extracted seven times with methylene chloride/methanol, 4:1. The organic extracts were combined, dried, and evaporated to yield 1.23 g. (78%) of pure 3-amino-4-carboxy-2-methylthiophene, m.p. 162°-164°. The compound was recrystallized from ethyl acetate/pentane to afford an analytical sample, m.p. 163°-164°.

Similarly, 5.0 g. (0.021 mole) of 3-amino-4-carbomethoxy-2-isopropylthiophene hydrochloride was converted into 3.3 g. (84%) of 3-amino-4-carboxy-2-isopropylthiophene, m.p. 117°-118°.

Similarly, 1.41 g. (0.00708 mole) 3-amino-4-carbomethoxy-2-propylthiophene hydrochloride was converted into 0.625 g. (48%) of 3-amino-4-carboxy-2-propylthiophene, m.p. 144°-145°.

EXAMPLE 12

A solution of 1.03 g. (0.005 mole) of 3-amino-4-carbomethoxy-2-methylthiophene hydrochloride in 30 ml. water was treated with a solution of 0.45 g. potassium cyanate in 10 ml. water. A white solid separated. The mixture was extracted three times with methylene chloride. The organic extracts were combined dried, and evaporated to yield 0.82 g. (77%) of pure 4-[(aminocarbonyl)amino]-5-methyl-3-thiophenecarboxylic acid methyl ester. The compound could be recrystallized from ethyl acetate to give a white solid, m.p. 194°-195°.

The following examples 13–16 illustrate pharmaceutical compositions containing 3-amino-4-carbomethoxy-2-n-propylthiophene hydrochloride (active compound).

EXAMPLE 13

| Capsule Formulation | |
|---|---|
|  | Per Capsule |
| Active compound | 10 mg |
| Lactose, U.S.P. | 165 mg |
| Corn Starch, U.S.P. | 30 mg |
| Talc, U.S.P. | 5 mg |
|  | Total Weight 210 mg |

Procedure

1. Active compound, lactose and corn starch were mixed in a suitable mixer.
2. The mixture was further blended by passing through a Fitzpatrick Comminuting Machine with a 1A screen with knives forward.
3. The blended powder was returned to the mixer, the talc added and blended thoroughly.
4. The mixture was filled into 4 hard shell gelatin capsules on a Parke Davis capsulating machine. (Any similar type capsulating machine may be used).

EXAMPLE 14

| Capsule Formulation | |
|---|---|
| | Per Capsule |
| Active compound | 50 mg |
| Lactose, U.S.P. | 125 mg |
| Corn Starch, U.S.P. | 30 mg |
| Talc, U.S.P. | 5 mg |
| Total Weight | 210 mg |

Procedure

1. Active compound was mixed with lactose and corn starch in a suitable mixer.
2. The mixture was further blended by passing through a Fitzpatrick Comminuting Machine with a 1A screen with knives forward.
3. The blended powder was returned to the mixer, the talc added and blended thoroughly.
4. The mixture was filled into 4 hard shell gelatin capsules on a Parke Davis capsulating machine.

EXAMPLE 15

| Tablet Formulation | |
|---|---|
| | Per Tablet |
| Active compound | 25.00 mg |
| Dicalcium Phosphate Dihydrate, Unmilled | 175.00 mg |
| Corn Starch | 24.00 mg |
| Magnesium Stearate | 1.00 mg |
| Total Weight | 225.00 mg |

Procedure

1. Active compound and corn starch were mixed together and passed through an 00 screen in Model "J" Fitzmill with hammers forward.
2. This premix was then mixed with dicalcium phosphate and one-half of the magnesium stearate, passed through a 1A screen in Model "J" Fitzmill with knives forward, and slugged.
3. The slugs were passed through a 2A plate in a Model "D" Fitzmill at slow speed with knives forward, and the remaining magnesium stearate was added.
4. The mixture was mixed and compressed.

EXAMPLE 16

| Tablet Formulation | |
|---|---|
| | Per Tablet |
| Active compound | 100 mg |
| Lactose, U.S.P. | 202 mg |
| Corn Starch, U.S.P. | 80 mg |
| Amijel Bo11* | 20 mg |
| Calcium Stearate | 8 mg |
| Total Weight | 410 mg |

*A prehydrolyzed food grade corn starch. Any similar prehydrolyzed corn starch may be used.

Procedure

1. Active compound, lactose, corn starch, and Amijel B011 were blended in a suitable mixer.
2. The mixture was granulated to a heavy paste with water and the moist mass was passed through a 12 screen. It was then dried overnight at 110° F.
3. The dried granules were passed through a 16 screen and transferred to a suitable mixer. The calcium stearate was added and mixed until uniform.
4. The mixture was compressed at a tablet weight of 410 mg, using tablet punches having a diameter of approximately three-eight inch. (Tablets may be either flat or biconvex and may be scored if desired).

EXAMPLE 17

4-amino-5-ethyl-3-thiophenecarboxylic acid methyl ester hydrochloride

To a solution of 125 g. (1.02 mols) of methyl-3-mercaptopropionate in 75 ml. of dry methanol was added dropwise at 0° 249 ml. (1.122 mols) of 25% sodium methoxide/methanol (Aldrich). The resulting mixture was treated dropwise at 0° with 200 g. (1.02 mols) of ethyl-2-bromobutyrate in 75 ml. of dry methanol. The cooling bath was removed and the reaction stirred overnight at 25°. The mixture was concentrated and partitioned between water and methylene chloride. The organic extracts were dried and evaporated to yield 229 g. (96%) of 4-amino-5-ethyl-3-thiophenecarboxylic acid methyl ester hydrochloride as a colorless oil.

EXAMPLE 18

4-carbomethoxy-3-keto-2-ethyltetrahydrothiophene

To a suspension of 63.5 g. (1.176 mols) of sodium methoxide in 300 ml. of dry benzene was added dropwise at 25° 229 g. (0.98 mol) of 2-ethyl-3-thia-1,6-hexanedioic-1-ethyl-6-methyl ester in 200 ml. of dry benzene. The reaction mixture warms up during the addition. After stirring overnight at room temperature, the reaction was poured into 800 ml. of water, and the benzene layer was further extracted with 200 ml. of water. The aqueous phases were combined, carefully acidified with 6 N HCl, and extracted three times with methylene chloride/methanol, 5:1. The organic extracts were dried and evaporated to afford 149.7 g. (82%) of pure 4-carbomethoxy-3-keto-2-ethyltetrahydrothiophene as a colorless oil.

EXAMPLE 19

4-carbomethoxy-3-keto-2-ethyltetrahydrothiophene oxime

To a solution of 276.1 g. (1.47 mols) of 4-carbomethoxy-3-keto-2-ethyltetrahydrothiophene in 500 ml. of anhydrous pyridine was added in several portions 121.6 g. (1.176 mols) of hydroxylamine hydrochloride. The reaction was allowed to proceed for 20 hours at 25°, concentrated, and partitioned between methylene chloride/3 N HCl. The aqueous phase was backwashed two times with methylene chloride/methanol 5:1. The organic phases were dried and evaporated to afford 253 g. (82%) of pure 4-carbomethoxy-3-keto-2-ethyltetrahydrothiophene oxime as a pale yellow oil.

EXAMPLE 20

4-amino-5-ethyl-3-thiophenecarboxylic acid methyl ester hydrochloride

A solution of 253 g. (1.25 mols) of 4-carbomethoxy-3-keto-2-ethyltetrahydrothiophene oxime in 2 l. of anhydrous ether was treated at 25° with a stream of gaseous hydrogen chloride for one hour. The reaction was seeded with 0.5 g. of authentic product and stirred overnight at 25°. The crude product was filtered, washed with anhydrous ether, and recrystallized from methanol/ether to afford 173 g. (62%) of 4-amino-5-ethyl-3-thiophenecarboxylic acid methyl ester hydrochloride, m.p. 164°.

In subsequent experiments, the ester hydrochloride was recrystallized from methanol/acetonitrile to afford pure 4-amino-5-ethyl-3-thiophenecarboxylic acid methyl ester hydrochloride, m.p. 174°–175°.

EXAMPLE 21

4-amino-5-ethyl-3-thiophenecarboxylic acid

A sample of 10.0 g. (0.0452 mole) of 4-amino-5-ethyl-3-thiophenecarboxylic acid methyl ester hydrochloride in 100 ml. methanol was treated with 105 ml. 1 N sodium hydroxide and heated under reflux for one hour. The resulting mixture was cooled and partitioned between water (pH 4.5) and methylene chloride/methanol (4:1). The aqueous phase was further extracted with methylene chloride/methanol (4:1) five additional times. The organic extracts were combined, dried over sodium sulfate and evaporated to yield 6.4 g. (81%) of 4-amino-5-ethyl-3-thiophenecarboxylic acid. The product was recrystallized from ethyl acetate/pentane to yield a pure sample, m.p. 132°–133° C.

EXAMPLE 22

4-amino-5-ethyl-3-thiophenecarboxylic acid ethyl ester hydrochloride

A sample of 1.10 g. (64.2 mmols) of 4-amino-5-ethyl-3-thiophenecarboxylic acid was dissolved in 20 ml. absolute ethanol which had been previously saturated with gaseous hydrogen chloride. The resulting reaction was heated under reflux for 22 hours, cooled and evaporated to afford 1.081 g. (71%) of pure 4-amino-5-ethyl-3-thiophenecarboxylic acid ethyl ester hydrochloride, m.p. 142°–143° C. (absolute ethanol).

EXAMPLE 23

4-amino-5-propyl-3-thiophenecarboxylic acid ethyl ester hydrochloride

A sample of 1.50 g. (8.097 mmols) of 4-amino-5-propyl-3-thiophenecarboxylic acid was dissolved in 75 ml. absolute ethanol which had been previously saturated with gaseous hydrogen chloride. The resulting reaction was heated under reflux for 24 hours, cooled and evaporated to afford 1.43 g. (71%) of pure 4-amino-5-propyl-3-thiophenecarboxylic acid ethyl ester hydrochloride, m.p. 144° C. (dec.) after recrystallization from ethyl acetate.

EXAMPLE 24

4-amino-5-ethyl-3-thiophenecarboxylic acid isopropyl ester hydrochloride

A sample of 1.02 g. (4.610 mmols) of 4-amino-5-ethyl-3-thiophenecarboxylic acid was dissolved in 50 ml. of isopropanol which had been previously saturated with gaseous hydrogen chloride. The resulting reaction was heated under reflux for 48 hours, cooled and evaporated to afford 0.927 g. (81%) of pure 4-amino-5-ethyl-3-thiophenecarboxylic acid isopropyl ester hydrochloride, m.p. 159° C. (dec.) after recrystallization from isopropanol/ether.

EXAMPLE 25

2-butyl-3-thia-1,6-hexanedioic-1-ethyl-6-methyl ester

To a solution of 106.8 g. (0.89 mol) of methyl-3-mercaptopropionate in 100 ml. dry methanol at 0° C. was added dropwise 193 ml. (0.98 mol) of a 25% solution of sodium methoxide in methanol. To the resulting mixture 200 g. (0.89 mol) of ethyl-2-bromovalerate in 100 ml. dry methanol was added dropwise at 0° C. The reaction was allowed to proceed at 25° C., overnight. After evaporation of the solvent, the residue was partitioned between water/methylene chloride, and the aqueous phase was further extracted (2x) with methylene chloride/methanol (4:1). The organic extracts were dried over sodium sulfate and evaporated to yield 213.25 g. (92%) of pure 2-butyl-3-thia-1,6-hexanedioic-1-ethyl-6-methyl ester as a colorless oil.

EXAMPLE 26

4-carbomethoxy-3-keto-2-butyltetrahydrothiophene

A solution of 213.25 g. (0.81 mol) of 2-butyl-3-thia-1,6-hexanedioic-1-ethyl-6-methyl ester in 400 ml. dry benzene was added dropwise to a suspension of 48.0 g. (0.89 mol) of anhydride sodium methoxide in 200 ml. dry benzene. The resulting mixture was stirred overnight at room temperature. The reaction was partitioned between water/ether, and the aqueous phase was further extracted with benzene (1x). After acidification to pH 1 with concentrated hydrochloric acid, the aqueous phase was extracted (3x) with methylene chloride. The organic extracts were combined, dried over sodium sulfate and evaporated to yield 96.5 g. (55%) of pure 4-carbomethoxy-3-keto-2-butyltetrahydrothiophene as a colorless oil.

EXAMPLE 27

4-carbomethoxy-3-keto-2-butyltetrahydrothiophene oxime

A sample of 96.5 g. (0.45 mol) of 4-carbomethoxy-3-keto-2-butyltetrahydrothiophene in 170 ml. pyridine was treated with 37.3 g. (0.54 mol) hydroxylamine hydrochloride and stirred overnight at 25° C. The resulting reaction was concentrated in vacuo and partitioned between 3 N hydrochloride acid/methylene chloride. The aqueous phase was further extracted (2x) with methylene chloride/methanol (4:1). The organic extracts were combined, dried over sodium sulfate and evaporated to afford 101 g. (97%) of pure 4-carbomethoxy-3-keto-2-butyltetrahydrothiophene oxime as a colorless oil.

EXAMPLE 28

4-amino-5-butyl-3-thiophenecarboxylic acid methyl ester hydrochloride

A sample of 101 g. (0.437 mol) of pure 4-carbomethoxy-3-keto-2-butyltetrahydrothiophene oxime was dissolved in 600 ml. absolute ether. Gaseous hydrogen chloride was introduced at 0° C. over the course of one hour. The resulting reaction was stirred overnight at 25° C. and evaporated to afford 109 g. (100%) of crude 4-amino-5-butyl-3-thiophenecarboxylic acid methyl ester hydrochloride. The product was purified by recrystallization from ethyl acetate/pentane to afford a white solid, m.p. 120° C. (dec.).

EXAMPLE 29

4-acetamido-5-ethyl-3-thiophenecarboxylic acid methyl ester

A solution of 11.085 g. (0.05 mol) of 4-amino-5-ethyl-3-thiophenecarboxylic acid methyl ester hydrochloride in 50 ml. anhydride pyridine was treated with 6.0 ml.

acetic anhydride in one portion at 25° C. The resulting reaction was stirred at room temperature for 3.0 hours, concentrated, and partitioned between 1 N hydrochloric acid methylene chloride. The aqueous phase was further extracted (2x) with methylene chloride. The organic extracts were combined, dried over sodium sulfate and evaporated to yield 11.17 g. (98%) of pure 4-acetamido-5-ethyl-3-thiophenecarboxylic acid methyl ester, m.p. 85°-86° C. (benzene/hexane).

EXAMPLE 30

5-ethyl-4-ethylaminothiophene-3-carboxylic acid methyl ester hydrochloride

A solution of 7.4 g. (0.0326 mol) of 4-acetamido-5-ethyl-3-thiophenecarboxylic acid methyl ester in 70 ml. absolute tetrahydrofuran was treated dropwise with 52 ml. of a 1 N diborane/tetrahydrofuran solution at 25° C. The reaction was stirred overnight at room temperature, quenched with water (dropwise) and partitioned between concentrated ammonium hydroxide/methylene chloride. The aqueous phase was further extracted (2x) with methylene chloride/methanol (4:1). The organic extracts were combined, dried over sodium sulfate and evaporated to yield 7.3 g. of residue. The residue was chromatographed over a one kilogram silica gel column eluting with chloroform/methanol (9:1). 5-ethyl-4-ethylaminothiophene-3-carboxylic acid methyl ester was eluted first and was obtained as a colorless oil by evaporating the appropriate fractions. This compound was then taken up in 50 ml. methanol which had been previously saturated with gaseous hydrogen chloride. Evaporation yielded 1.37 g. (17%) of pure 5-ethyl-4-ethylaminothiophene-3-carboxylic acid methyl ester hydrochloride, m.p. 135° C. (dec.) (methanol/ether).

EXAMPLE 31

5-ethyl-4-trifluoroacetamidothiophene-3-carboxylic acid methyl ester

A solution of 4.434 g. (0.02 mol) of 4-amino-5-ethyl-3-thiophenecarboxylic acid methyl ester, hydrochloride in 40 ml. anhydride pyridine was treated at 25° C. with 3.14 ml. trifluoroacetic anhydride in one portion. The resulting reaction was stirred at 25° C. for one hour and partitioned between 3 N hydrochloric acid/methylene chloride. The aqueous phase was further extracted (2x) with methylene chloride/methanol, (4:1). The organic extracts were combined, dried over sodium sulfate and evaporated to afford 4.85 g. (86%) of pure 5-ethyl-4-trifluoroacetamidothiophene-3-carboxylic acid methyl ester, m.p. 55°-56° C. (hexane).

EXAMPLE 32

5-ethyl-4-methylamino-3-thiophenecarboxylic acid methyl ester hydrochloride

A solution of 2.81 g. (0.010 mol) of 5-ethyl-4-trifluoroacetamidothiophene-3-carboxylic acid methyl ester in 30 ml. absolute tetrahydrofuran was added dropwise at 0° C. to a flask containing 1.32 g. of sodium hydride (50% dispersion) in 30 ml. absolute tetrahydrofuran and 5 ml. of methyl iodide. The resulting reaction was stirred for 1.5 hours and treated sequentially with 1.3 g. sodium hydride (50%) and 5 ml. methyl iodide. After 6 hours, the resulting reaction was quenched with 25 ml. of a 20% ammonium hydroxide solution which was added dropwise. The reaction mixture was acidified with concentrated hydrochloric acid and washed (2x) with methylene chloride. The aqueous phase was made basic with concentrated ammonium hydroxide and extracted (3x) with methylene chloride/methanol (4:1). The organic extracts were combined, dried over sodium sulfate and evaporated to yield 0.734 g. of 5-ethyl-4-methylamino-3-thiophenecarboxylic acid methyl ester, as a colorless oil. This compound was dissolved in 20 ml. of methanol which had been previously saturated with gaseous hydrogen chloride and evaporated to yield 0.868 g. (37%) of crude 5-ethyl-4-methylamino-3-thiophenecarboxyic acid methyl ester hydrochloride. The product was purified by recrystallization from methanol ether to afford white needles, m.p. 172°-173°.

EXAMPLE 33

TABLE VI

EFFECT OF ORAL ADMINISTRATION OF COMPOUND A AT INCREASING CONCENTRATIONS ON HEPATIC FATTY ACID AND CHOLESTEROL SYNTHESIS[a]

| | Fatty Acid Synthesis | | Cholesterol Synthesis | |
|---|---|---|---|---|
| | $\mu$moles $^3H_2O$/g/30 min | nmoles[$^{14}C$]alanine/g/30 min | $\mu$moles $^3H_2O$/g/30 min | mmoles[$^{14}C$]alanine/g/30 min |
| Control | | | | |
| (1% gum arabic) | 36.7 ± 2.7 | 685 ± 59 | 0.50 ± 0.06 | 13.9 ± 1.5 |
| Compound A | 18.0 ± 2.3*** | 290 ± 49** | 0.60 ± 0.06 | 15.8 ± 1.6 |
| | (49%) | (42%) | (120%) | (114%) |

[a]Charles River female rats were fasted 48 hr, then meal-fed (8 to 11 a.m.) a high carbohydrate diet for 14 days. Rats weighing 180 to 210 g (10 in each group) were dosed by gastric gavage, with either 1% gum arabic or Compound A in 1% gum arabic. The initial dose was 0.4 mmoles (89 mg) per kg body weight and was increased by 0.2 mmoles (44 mg) per kg body weight every other day. The experimental period consisted of 10 days, and the doses given were 0.4, 0.6, 0.8, 1.0 and 1.2 mmoles per kg. All rats were fed ½ hr after the oral dose. On the 10th day, following the 3 hr meal, each rat received an intravenous injection (consisting of 5 $\mu$Ci [U-$^{14}C$]alanine, 1 mCi $^3H_2O$, 12.3 mg alanine and 30.6 mg α-ketoglutaric acid) and was killed 30 min later. Livers were quickly excised, saponified, and extracted for fatty acids or cholesterol. Data are expressed as $\mu$moles $^3H_2O$ or nmoles [$^{14}C$]alanine converted into fatty acids or cholesterol per gram liver per 30 min.
Each value is the mean ± SE.
***$p < 0.05$
Compound A is 4-amino-5-ethyl-3-thiophenecarboxylic acid methyl ester hydrochloride.

EXAMPLE 34

TABLE VII

EFFECT OF ORAL ADMINISTRATION OF COMPOUND A AT INCREASING CONCENTRATIONS ON SERUM TRIGLYCERIDES, CHOLESTEROL INSULIN AND GLUCOSE[a]

| | Triglycerides mg % | Cholesterol mg % | Insulin ng/ml | Glucose mg % |
|---|---|---|---|---|
| Control | | | | |
| (1% gum arabic) | 51 ± 3 | 97 ± 5 | 3.85 ± 0.74 | 165 ± 7 |
| Compound | 31 ± 3*** | 79 ± 6* | 1.91 ± 0.24* | 160 ± 5 |

TABLE VII-continued
EFFECT OF ORAL ADMINISTRATION OF COMPOUND A AT INCREASING CONCENTRATIONS ON SERUM TRIGLYCERIDES, CHOLESTEROL INSULIN AND GLUCOSE[a]

| | Triglycerides mg % | Cholesterol mg % | Insulin ng/ml | Glucose mg % |
|---|---|---|---|---|
| A | (62%) | (81%) | (49%) | (97%) |

[a]Charles River female rats were fasted 48 hr, then meal-fed (8 to 11 a.m.) a high carbohydrate diet for 14 days. Rats weighing 180 to 210 g (10 in each group) were dosed by gastric gavage, with either 1% gum arabic or Compound A in 1% gum arabic. The initial dose was 0.4 mmoles (89 mg) per kg body weight and was increased by 0.2 mmoles (44 mg) per kg body weight every other day. The experimental period consisted of 10 days, and the doses given were 0.4, 0.6, 0.8, 1.0 and 1.2 mmoles per kg. All rats were fed ½ hr after the oral dose. On the 10th day, following the 3 hr meal, each rat received an intravenous injection (consisting of 5 μCi [U-$^{14}$C]alanine, 1 mCi $^3$H$_2$O, 12.3 mg alanine and 30.6 mg α-ketoglutaric acid) and was killed 30 min later. Blood was collected, allowed to clot and serum analyzed. Each value is the mean ±SE
*p < 0.05
***p < 0.001
Compound A is 4-amino-5-ethyl-3-thiophenecarboxylic acid methyl ester hydrochloride.

EXAMPLE 35

The antiobesity activity of 4-amino-5-ethyl-3-thiophene carboxylic acid methyl ester hydrochloride (Compound A) was evaluated in a long-term chronic experiment in which body weight gain and food consumption were monitored at least biweekly. The study was conducted on Charles River rats receiving 10% corn oil: 60% glucose (high fat) diets. For the first 32 days of this study a dose of approximately 71 mg./kg. body weight/day was given. From day 33 until the end of the study the average daily dose was increased to 130 mg./kg. body weight/day. The study included a group of rats pair-fed to the Compound A treated rats, i.e., the pair-fed animals received the same amount of food as their Compound A paired rat consumed on the previous day. Pair feeding was terminated several days after food intake in the Compound A treated groups returned to control levels. Pair-feeding to the Compound A treated group was terminated on day 22. Upon termination of the study, carcass lipid and protein levels, serum lipids and hepatic rates of fatty acid synthesis in vivo were determined. A summary of the initial and final body weights, cumulative weight gained and food consumed and average daily food intake is presented in Table VIII. A summary of the effect of Compound A on body fat and protein is presented in Table IX.

TABLE VIII
EFFECT OF COMPOUND A ADMINISTERED AS A DIETARY ADMIXTURE IN 10% CORN OIL DIET ON BODY WEIGHT AND FOOD INTAKE IN AD LIBITUM FED CHARLES RIVER RATS IN A 63 DAY STUDY[a,b]

| Treatment | IBW g | FBW g | CBWG g | CFC g | FI g/day | Drug Ingested[c] mmoles(mg)/kg/day |
|---|---|---|---|---|---|---|
| Control | 215 ± 3 | 282 ± 8 | 68 ± 6 | 1115.1 ± 44.1 | 17.7 ± 0.7 | — |
| Pair-Fed | 214 ± 3 | 281 ± 6 | 66 ± 6 | 1008.0 ± 25.2* | 16.0 ± 0.4* | — |
| Compound A | 214 ± 3 | 256 ± 4* | 41 ± 4* | 1026.9 ± 25.2 | 16.3 ± 0.4 | .320 (71) .586 (130) |

[a]Female Charles River rats (10 rats per group) were fed ad libitum the 10% corn oil:60% glucose diet. On day 1 of the experiment rats were divided into three groups: (1) control, (2) Compound A as a dietary admixture (71 mg/kg body weight/day, and (3) pair-fed to the Compound A treated group. Pair-feeding was terminated on day 23. On day 33 the concentraton of Compound A was increased to 130 mg/kg/day.
[b]Abbreviations:
IBW = initial body weight;
FBW = final body weight;
CBWG = cumulative body weight gain;
CFC = cumulative food consumption; and
FI = food intake.
*p ≦ 0.05
Compound A is 4-amino-5-ethyl-3-thiophene carboxylic acid methyl ester hydrochloride.

TABLE IX
EFFECT OF COMPOUND A ADMINISTERED AS A DIETARY ADMIXTURE IN 10% CORN OIL DIET ON TOTAL BODY FAT AND PROTEIN IN AD LIBITUM FED CHARLES RIVER RATS (63 DAY STUDY)[a]

| | Lipid | | Protein | |
|---|---|---|---|---|
| Treatment | total (g) | % of body weight | total (g) | % of body weight |
| Control | 66.8 ± 7.1 | 23.5 ± 2.2 | 54.1 ± 4.8 | 19.1 ± 1.6 |
| Compound A | 42.1 ± 4.5* | 16.5 ± 1.7* | 52.7 ± 0.6 | 20.7 ± 1.4 |

[a]Female Charles River rats (10 rats per group) were fed ad libitum the 10% corn oil:60% glucose diet. On day 1 of the experiment rats were divided into three groups: (1) control, (2) Compound A as a dietary admixture (71 mg/kg body weight/day), and (3) pair-fed to the Compound A treated group. Pair-feeding was terminated on day 22. On day 33 the concentration of Compound A was increased to 130 mg/kg/day.
*p ≦ 0.05
Compound A is 4-amino-5-ethyl-3-thiophene carboxylic acid methyl ester hydrochloride.

The following Examples 36–41 illustrate pharmaceutical compositions having 4-amino-5-ethyl-3-thiophene carboxylic acid methyl ester hydrochloride (Active Compound) as the active ingredient.

EXAMPLE 36

TABLET FORMULATIONS: (Direct Compression)

| Item | Ingredients | mg/tablet | mg/tablet | mg/tablet |
|---|---|---|---|---|
| 1. | Active Compound | 15 | 30 | 60 |
| 2. | Lactose | 207 | 192 | 162 |
| 3. | Avicel | 45 | 45 | 45 |
| 4. | Direct Compression Starch | 30 | 30 | 30 |
| 5. | Magnesium Stearate | 3 | 3 | 3 |
| | Weight of tablet | 300 mg | 300 mg | 300 mg |

Procedure (1) Mix Item 1 with equal amount of lactose. Mix well.

(2) Mix with Item 3, 4, and remaining amount of Item 2. Mix well.
(3) Add magnesium stearate and mix for 3 minutes.
(4) Compress on a suitable punch.

EXAMPLE 37

| | CAPSULE FORMULATION | | | |
|---|---|---|---|---|
| Item | Ingredients | mg/capsule | mg/capsule | mg/capsule |
| 1 | Active Compound | 15 | 30 | 60 |
| 2 | Lactose | 239 | 224 | 194 |
| 3 | Starch | 30 | 30 | 30 |
| 4 | Talc | 15 | 15 | 15 |
| 5 | Magnesium Stearate | 1 | 1 | 1 |
| | Capsule fill weight | 300 mg | 300 mg | 300 mg |

Procedure

1. Mix items 1–3 in a suitable mixer.
2. Add talc and magnesium stearate and mix for a short period of time.

Encapsulate on an appropriate encapsulation machine.

EXAMPLE 38

| | TABLET FORMULATIONS: (Wet Granulation) | | | |
|---|---|---|---|---|
| Item | Ingredients | mg/tablet | mg/tablet | mg/tablet |
| 1. | Active Compound | 15 | 30 | 60 |
| 2. | Lactose | 188 | 173 | 188 |
| 3. | Modified Starch | 25 | 25 | 30 |
| 4. | Pregelatinized Starch | 20 | 20 | 20 |
| 5. | Distilled Water q.s. | — | — | — |
| 6. | Magnesium Stearate | 2 | 2 | 2 |
| | Weight of tablet | 250 mg | 250 mg | 250 mg |

Procedure

1. Mix Items 1–4 in a suitable mixer.
2. Granulate with sufficient distilled water to proper consistency. Mill.
3. Dry in a suitable oven.
4. Mill and mix with magnesium stearate for 3 minutes.
5. Compress on a suitable press equipped with appropriate punches.

EXAMPLE 39

| | CAPSULE FORMULATION | | | |
|---|---|---|---|---|
| Item | Ingredient | mg/capsule | mg/capsule | mg/capsule |
| 1. | Active Compound | 100 | 250 | 500 |
| 2. | Lactose | 99 | 148 | — |
| 3. | Corn starch | 20 | 30 | 57 |
| 4. | Talc | 5 | 10 | 15 |
| 5. | Magnesium stearate | 1 | 2 | 3 |
| | Fill weight of capsule | 225 | 440 | 575 |

Procedure

1. Mix items 1, 2, and 3 in a suitable mixer. Mill through a suitable mill.
2. Mix the mixture in Step 1 with item 4 and 5 and fill on a suitable machine.

EXAMPLE 40

| | TABLET FORMULATIONS: (Wet Granulation) | | | |
|---|---|---|---|---|
| Item | Ingredient | mg/tablet | mg/tablet | mg/tablet |
| 1. | Active Compound | 100 | 250 | 500 |
| 2. | Lactose | 147.5 | 100 | 97.5 |
| 3. | Pregelatinized starch | 25 | 30 | 60 |
| 4. | Modified starch | 25 | 50 | 60 |
| 5. | Corn starch | 25 | 50 | 60 |
| 6. | Magnesium stearate | 2.5 | 5 | 7.5 |
| | Weight of tablet | 325 | 500 | 785 |

Procedure

1. Mix items 1, 2, 3, 4 and 5 in a suitable mixer, granulate with water, and dry over night in a suitable oven. Mill through suitable mill.
2. Mix with item 6 and compress on a suitable press.

EXAMPLE 41

| | TABLET FORMULATIONS: (Wet Granulation) | | | |
|---|---|---|---|---|
| Item | Ingredient | mg/tablet | mg/tablet | mg/tablet |
| 1. | Active Compound | 100 | 250 | 500 |
| 2. | Lactose | 98.5 | 147.5 | 170 |
| 3. | Polyvinyl pyrrolidone | 15 | 30 | 40 |
| 4. | Modified starch | 15 | 30 | 40 |
| 5. | Corn starch | 15 | 30 | 40 |
| 6. | Magnesium stearate | 1.5 | 2.5 | 5 |
| | Weight of tablet | 245 mg | 490 mg | 795 mg |

Procedure (1) Mix items 1, 2, 4 and 5 in a suitable mixer, granulate with PVP and dissolve in water/alcohol. Dry the granulation. Mill the dry granulation through a suitable mill.
(2) Add magnesium stearate and compress on a suitable press.

EXAMPLE 42

4-carbomethoxy-3-keto-2-ethyltetrahydrothiophene

To a suspension of 63.5 g. (1.176 mols) of sodium methoxide in 300 ml. of dry toluene was added dropwise at 25° 229 g. (0.98 mol) of 2-ethyl-3-thia-1,6-hexanedioic-1-ethyl-6-methyl ester in 200 ml. of dry toluene. The reaction mixture warms up during the addition. After stirring overnight at room temperature, the reaction was poured into 800 ml. of water, and the toluene layer was further extracted with 200 ml. of water. The aqueous phases were combined, carefully acidified with 6 N HCl, and extracted three times with methylene chloride/methanol, 5:1. The organic extracts were dried and evaporated to afford 149.7 g. (82%) of pure 4-carbomethoxy-3-keto-2-ethyltetrahydrothiophene as a colorless oil.

EXAMPLE 43

4-carbomethoxy-3-keto-2-ethyltetrahydrothiophene oxime

To a solution of 507 g. (2.697 mols) of 4-carbomethoxy-3-keto-2-ethyltetrahydrothiophene in 327 ml. of anhydrous pyridine was added in several portions 206.1 g. (2.967 mols) of hydroxylamine hydrochloride. The reaction was allowed to proceed for 20 hours at 25° and partitioned between methylene chloride/6 N HCl. The aqueous phase was backwashed two times with methylene chloride/methanol 5:1. The organic phases were dried and evaporated to afford 544.5 g. (99%) of pure 4-carbomethoxy-3-keto-2-ethyltetrahydrothiophene oxime as a pale yellow oil.

EXAMPLE 44

4-amino-5-ethyl-3-thiophenecarboxylic acid methyl ester hydrochloride

A solution of 544.48 g. (2.682 mol) of 4-carbomethoxy-3-keto-2-ethyltetrahydrothiophene oxime in 0.5 l. of anhydrous ether was added (mechanical stirring) over 20 minutes to a 2.0 l. solution of gaseous hydrogen chloride in ether (saturated). The reaction was seeded with 10.0 mg. of authentic product, thus inducing crystallization. The reaction was allowed to run for 20 hours at 25° and the product, which separated, was filtered off and washed well with anhydrous ether. This procedure yields 423 g. (71%) of 4-amino-5-ethyl-3-thiophenecarboxylic acid methyl ester hydrochloride, m.p. 174°–175° (methanol/acetonitrile).

We claim:

1. A process for reducing blood lipid levels in warm blooded animals which comprises administering an amount of a compound of the formula:

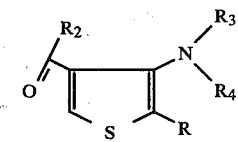

wherein R is lower alkyl; $R_2$ is hydrogen, hydroxy, lower alkoxy, or amino; $R_3$ and $R_4$ individually are lower alkyl, aryl, aralkyl or hydrogen; or a pharmaceutically acceptable salt thereof, in an amount effective for reducing blood lipid levels.

2. The process of claim 1 wherein said compound is:

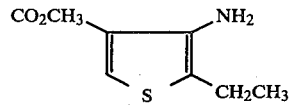

or a pharmaceutically acceptable salt thereof.

3. A method for reducing body fat in warm-blooded animals comprising administering a compound of the formula:

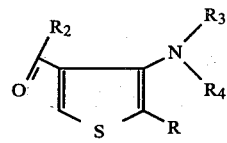

wherein R is lower alkyl; $R_2$ is hydrogen, hydroxy, lower alkoxy, or amino; $R_3$ and $R_4$, which may be the same or different, are lower alkyl, aryl, aralkyl, acyl and hydrogen; or a pharmaceutically acceptable salt thereof, in an amount which is effective as an anti-obesity agent.

4. The method of claim 3 wherein the compound is

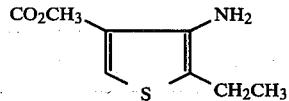

or a pharmaceutically acceptable salt thereof.

5. The process of claim 2 wherein the compound is 4-amino-5-ethyl-3-thiophene carboxylic acid methyl ester.

6. The process of claim 2 wherein the pharmaceutically acceptable salt is 4-amino-5-ethyl-3-thiophene carboxylic acid methyl ester hydrochloride.

7. The process of claim 1 wherein the compound is 4-amino-5-ethyl-3-thiophene carboxylic acid.

8. The method of claim 4 wherein the compound is 4-amino-5-ethyl-3-thiophene carboxylic acid methyl ester.

9. The method of claim 4 wherein the pharmaceutically acceptable salt is 4-amino-5-ethyl-3-thiophene carboxylic acid methyl ester hydrochloride.

10. The method of claim 3 wherein the compound is 4-amino-5-ethyl-3-thiophene carboxylic acid.

* * * * *